(12) United States Patent
Ryan et al.

(10) Patent No.: US 7,118,595 B2
(45) Date of Patent: *Oct. 10, 2006

(54) FLEXIBLE ANNULOPLASTY PROSTHESIS AND HOLDER

(75) Inventors: Timothy R Ryan, Shorewood, MN (US); Joseph C. Morrow, Eden Prairie, MN (US); Carlos G. Duran, Missoula, MT (US)

(73) Assignee: Medtronic, Inc., Minneapolis, MN (US)

( * ) Notice: Subject to any disclaimer, the term of this patent is extended or adjusted under 35 U.S.C. 154(b) by 211 days.

This patent is subject to a terminal disclaimer.

(21) Appl. No.: 10/174,199

(22) Filed: Jun. 19, 2002

(65) Prior Publication Data

US 2003/0176917 A1    Sep. 18, 2003

Related U.S. Application Data

(63) Continuation-in-part of application No. 10/100,044, filed on Mar. 18, 2002, now Pat. No. 6,719,786.

(51) Int. Cl.
*A61F 2/24* (2006.01)
*A61F 11/00* (2006.01)

(52) U.S. Cl. ..................... 623/2.11; 623/904
(58) Field of Classification Search ............. 623/2.11, 623/2.26, 2.36, 2.4, 2.41
See application file for complete search history.

(56) References Cited

U.S. PATENT DOCUMENTS

| | | | |
|---|---|---|---|
| 3,656,185 A | 4/1972 | Carpentier | |
| 3,828,787 A | 8/1974 | Anderson et al. | |
| 4,042,979 A | 8/1977 | Angell | |
| 4,055,861 A | 11/1977 | Carpentier et al. | |
| 4,106,129 A | 8/1978 | Carpentier et al. | |
| 4,185,636 A | 1/1980 | Gabbay et al. | |
| 4,204,283 A | 5/1980 | Bellhouse et al. | |
| 4,290,151 A | 9/1981 | Massana | |
| 4,306,319 A | 12/1981 | Kaster | |
| 4,535,483 A | 8/1985 | Klawitter et al. | |
| 4,612,011 A | 9/1986 | Kautzky | |

(Continued)

FOREIGN PATENT DOCUMENTS

AU          464075          8/1975

(Continued)

OTHER PUBLICATIONS

Carpentier-Edwards Physio Annuloplasty Ring, "Technical Product Manual," Baxter (1996) (22 pages).

(Continued)

*Primary Examiner*—Corrine McDermott
*Assistant Examiner*—William H Matthews
(74) *Attorney, Agent, or Firm*—Jeffrey J. Hohenshell

(57) ABSTRACT

A valve repair system, preferably including an annuloplasty prosthesis and a holder for the prosthesis. The holder includes a first component having a central opening, a circumferential surface and an outwardly extending member. The annuloplasty prosthesis is located adjacent to the circumferential surface, above the outwardly extending member. The holder further includes a second component movable upwardly relative to the first holder component and includes a rigid penetrating member extending downward from the second component into the prosthesis, holding it adjacent the circumferential surface. The holder also includes a suturing guide for assisting a physician in valve repair surgery, which may be a cuttable suture extending across the central opening along a path approximating a desired line of leaflet coaption. The cuttable suture may additionally secure the first and second components to one another. The suturing guide may also be incorporated into one-piece annuloplasty prosthesis holders or into stand-alone tools that do not carry annuloplasty prostheses.

19 Claims, 10 Drawing Sheets

U.S. PATENT DOCUMENTS

| | | | |
|---|---|---|---|
| 4,743,253 A | 5/1988 | Magladry | |
| 4,755,181 A | 7/1988 | Igoe | |
| 4,865,600 A | 9/1989 | Carpentier et al. | |
| 4,911,164 A | 3/1990 | Roth | |
| 4,932,965 A | 6/1990 | Phillips | |
| 5,011,481 A * | 4/1991 | Myers et al. | 606/1 |
| 5,104,407 A | 4/1992 | Lam et al. | |
| 5,350,420 A | 9/1994 | Cosgrove et al. | |
| 5,415,667 A | 5/1995 | Frater | |
| 5,522,884 A * | 6/1996 | Wright | 623/2.11 |
| 5,984,959 A | 11/1999 | Robertson et al. | |
| 6,183,512 B1 | 2/2001 | Howanec, Jr. et al. | |
| 6,283,993 B1 * | 9/2001 | Cosgrove et al. | 623/2.11 |
| 6,319,280 B1 | 11/2001 | Schoon | |
| 6,332,893 B1 | 12/2001 | Mortier et al. | |
| 6,406,492 B1 | 6/2002 | Lytle | |
| 6,409,758 B1 | 6/2002 | Stobie et al. | |
| 6,702,852 B1 | 3/2004 | Stobie et al. | |
| 6,719,786 B1 * | 4/2004 | Ryan et al. | 623/2.11 |
| 6,786,924 B1 | 9/2004 | Ryan et al. | |
| 6,955,689 B1 | 10/2005 | Ryan et al. | |
| 2001/0049558 A1 | 12/2001 | Liddicoat et al. | |
| 2004/0024451 A1 | 2/2004 | Johnson et al. | |
| 2004/0186564 A1 | 9/2004 | Ryan et al. | |
| 2005/0197696 A1 | 9/2005 | Duran | |

FOREIGN PATENT DOCUMENTS

| | | |
|---|---|---|
| GB | 2083362 | 3/1982 |
| GB | 2108393 | 5/1993 |
| WO | WO 00/59408 | 10/2000 |

OTHER PUBLICATIONS

Ian J. Reece, M.B., F.R.C.S., et al, "Surgical Treatment of Mitral Systolic Click syndrome: Results in 37 Patients," The Annals of Thoracic Surgery, vol. 39, No. 2, Feb. 1985 (pp. 155-158).

Denton A. Cooley, M.D., et al, "Mitral Leaflet Prolapse: Surgical Treatment Using a Posterior Annular Collar Prosthesis," Cardiovascular Diseases, Bulletin of the Texas Heart Institute, vol. 3, Nov. 4, 1976 (pp. 438-439; 442-443).

Surgical Techniques for the Repair of Anterior Mitral Leaflet Prolapse/ Carlos M.G. Duran, M.D., Ph.D./J Card Surg 1999; 14:471-481.

Medtronic Booklet "Medtronic Duran Flexible Annuloplasty Systems In-Service Guide"/ UC200004685 EN.

* cited by examiner

FLEXIBLE ANNULOPLASTY PROSTHESIS AND HOLDER

This application is a continuation in part of application Ser. No. 10/100,444, filed Mar. 18, 2002 now U.S. Pat, No. 6,719,786.

BACKGROUND OF THE INVENTION

The present invention relates generally to surgical tools and more particularly for surgical tools used in conjunction with valve repair, including tools for holding prostheses such as annuloplasty rings and bands.

Annuloplasty rings and bands are useful in a variety of surgical procedures, including mitral and tricuspid annular reduction. In these procedures, sutures are first placed around all or portions of the valve annulus at spaced intervals. Sutures passing through the annulus in regions in which reduction of the valve annulus is desired are spaced equidistant from one another, for example, at 4 mm intervals. These sutures are then brought through the annuloplasty ring or band more closely spaced than where they pass through the annulus, for example, 2 mm. The process of passing the sutures through the ring or band occurs while the prosthesis is held above the valve annulus. The ring is then moved down into contact with the valve annulus, causing contraction of the annulus, thus effecting a reduction in valve annulus circumference. This basic procedure is used to correct both mitral and tricuspid annular dilatation.

In order for the sutures to be passed through the annuloplasty ring, it is desirable that the ring be held in a fixture or tool of some fashion. One early tool was manufactured by Pilling Instruments, and took the general form of a cone provided with a circumferential groove near the base. The cone was also provided with longitudinal slits, so that the tool could be contracted to accept the ring around the circumference of the groove. The tool was adapted to be held by means of a threaded handle.

More recent holder designs are disclosed in U.S. Pat. No. 6,283,993, wherein sutures passing through the prosthesis are used to retain it in a circumferential groove on the holder. An alternative design is disclosed in U.S. Pat. No. 5,011,481, which employs radially and downwardly extending fingers in conjunction with sutures passing around the prosthesis to retain it on the holder. Yet another alternative design is disclosed in U.S. Pat. No. 5,522,884, in which an adjustable annuloplasty ring is retained on its holder by tightening the adjusting sutures within the ring to contract it into a circumferential groove on the holder.

Examples of flexible annuloplasty bands and rings are also disclosed in the above cited patents, all of which are incorporated herein by reference in their entireties.

SUMMARY OF THE INVENTION

The present invention is directed toward an improved holder for use with annuloplasty prostheses. The holder is specifically configured to assist the surgeon in performing the technique of mitral or tricuspid reduction, and is typically provided in conjunction with the annuloplasty ring or band, ready for use. The holder takes the general form of an oblate ring component having an upper surface, a lower surface, a central opening and an outer circumferential surface corresponding generally to the configuration of a valve annulus. The prosthesis extends around at least a portion of this circumferential surface and is releasably retained alongside this surface during the passing of sutures through the prosthesis.

The present invention provides improvements directed to the mechanism for retaining the prosthesis on the holder during passage of the sutures and releasing the prosthesis after positioning on the valve annulus. Rather than retaining the annuloplasty ring to the holder by means of sutures passing through the annuloplasty ring, the ring is retained by means of downwardly extending penetrating members such as barbs, pins, pegs, or needles, which enter the annuloplasty prosthesis and retain it to the holder during passage of sutures through the prosthesis. These penetrating members may be fabricated of metal or molded plastic and are sufficiently rigid that they are not readily deflected outward to allow outward movement of the annuloplasty prosthesis away from the holder. The penetrating members may have sharpened or relatively blunt tips.

The preferred embodiment is a two-component holder in which the first component includes the circumferential surface around which the prosthesis is mounted and the second component carries the penetrating members. The first component also typically includes radially extending projections that prevent the prosthesis from moving downward off of the penetrating members, until upward movement of the second component. In a preferred embodiment, the first and second holder components are retained to one another, for example by means of a suture or sutures coupling the first and second components together. In this embodiment, the first and second components become movable relative to one another following cutting of the suture or sutures retaining them together. The first and second holder components are preferably molded of generally rigid plastics but might in some cases be fabricated of metal or other materials.

The present invention generally is intended to provide a simplified and more easily employed mechanism for holding the annuloplasty prosthesis during passage of the sutures through the prosthesis and for releasing it from the holder after the ring has been moved downward into its intended location on the valves annulus.

The holder of the present invention is also provided with a mechanism for assisting the surgeon in the surgical repair of broken or elongated chordae tendinae (chords), as is sometimes performed in conjunction with placement of an annuloplasty prosthesis. This is accomplished by means of a suturing guide extending across the central opening through the holder, approximating the line of leaflet coaption. Sutures used to reconnect the inner edges of the valve leaflets to the papillary muscles are knotted around the suturing guide and the leaflet edge, to assure that the length of the suture is appropriate to allow leaflet coaption.

The suture guide may be any elongated structure, such a rod, bar or cord, but in the preferred embodiment of the invention, the suture guide takes the form of a suture or sutures, extending across the opening through the holder. Cutting the suture allows it to be pulled through the knots at the leaflet edge, facilitating removal of the holder. In the disclosed embodiment, the suture or sutures extending across the central opening are extensions of sutures holding the first and second components closely adjacent one another, routed so that cutting the sutures to allow their removal from the knots at the leaflet edge also releases the first and second components so that the second component may move upward relative to the first component, allowing removal of the annuloplasty prosthesis from the holder.

While in the preferred embodiments described below, the suture guide is part of a two-component annuloplasty prosthesis holder, the suturing guide may also be incorporated in a one-piece holder or in a stand-alone tool which does not carry an annuloplasty prosthesis. In such embodiments, the tool could include a single ring-shaped component corresponding generally to the annulus of the valve to be repaired and the suturing guide could extend across the central opening through the ring shaped component in a manner analogous to its location in the disclosed preferred embodiments.

DETAILED DESCRIPTION OF THE PREFERRED EMBODIMENTS

Figure 1:
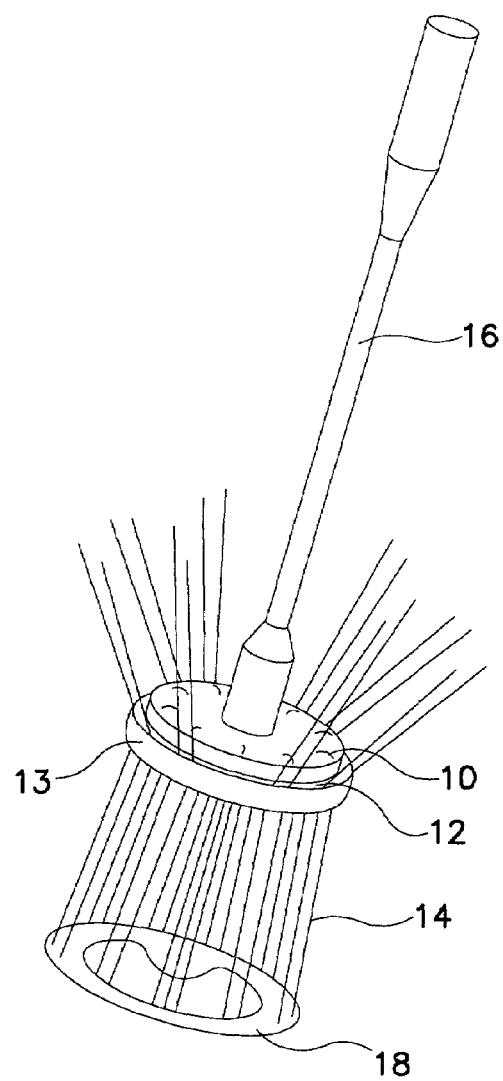
FIG. 1 illustrates a prior art annuloplasty prosthesis and holder, after passage of sutures through the annuloplasty prosthesis.

FIG. 1 is a perspective view of a two-piece annuloplasty holder according to the prior art. In particular, the holder system as illustrated is described in the brochure "Medtronic Duran Flexible Annuloplasty Systems In Service Guide", published by Medtronic, Inc. in 2000, Publication No. UC200004685 EN, incorporated herein by reference in its entirety. The holder system includes a handle 16 which may be made of metal or plastic, and which may, in some embodiments, include a malleable shaft allowing for manual reconfiguration of the shaft. The shaft is snapped into the holder itself, which includes two components 10 and 12 that are molded of rigid plastic. The upper component 10 of the holder is transparent and serves as a template, including markings illustrating the locations of the valve trigones and regularly spaced markings assisting in placement of sutures around the annuloplasty prosthesis 13. As illustrated, the first component 12 of the prosthesis releasably secured to the second component 10 of the prosthesis and the annuloplasty prosthesis 13 is mounted around a circumferential surface of the first holder component 12.

As illustrated, sutures 14 have been passed through the valve annulus 18 and upwardly and outwardly through the prosthesis 13 itself, according to conventional practice for implantation of annuloplasty prostheses. The holder system is then used to move the prosthesis 13 downwardly along the sutures so that it is seated adjacent to the upper surface of the annulus 18. The second component 10 of the holder may be removed from the first component 12 by cutting the sutures holding them together, leaving the ring mounted around the first holder component 12, seated adjacent the valve annulus. Although not visible in this view, the first component 12 of the holder includes a large central orifice, so that testing to assure that leaflets of the heart valve co-apt can be accomplished while the prosthesis 13 remains on the first component 12 of the holder. In the particular product marketed by Medtronic, Inc., removable of the prosthesis 13 from the first holder component 12 was accomplished by cutting sutures that held the prosthesis on the holder.

Figure 2:
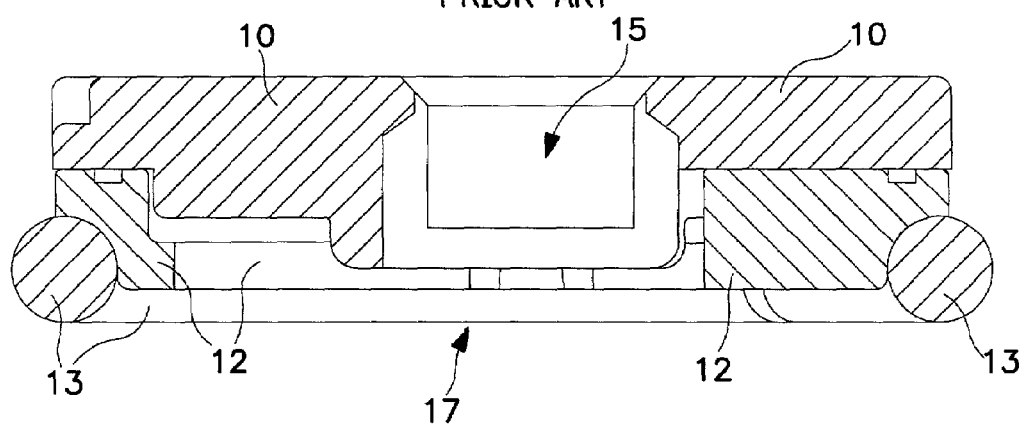
FIG. 2 illustrates a cross section through a prior art annuloplasty prosthesis holder.

FIG. 2 is a cross section through the first and second components of the holder illustrated in FIG. 1, in conjunction with attached annuloplasty prosthesis 13. In this view it can be seen that the second component 10 of the holder is provided with a formed recess 15 configured to releasably engage a handle 16 (FIG. 1). In this view also it can be seen that the first holder component 12 defines a large central aperture illustrated generally at 17, through which operation of the associated heart valve can be observed after removal of the second holder component 10. As noted above, component 10 is held to component 12 by means of cuttable sutures, and prosthesis 13 is likewise maintained mounted to component 12 by means of cuttable sutures. Mounting of the prosthesis 12 to the first component 12 of the holder by means of these sutures requires handwork, increasing the expense and complexity of production of the system comprising the holder and the prosthesis. In addition, release of the prosthesis 13 from the first holder 12 requires multiple cuts of the sutures holding the prosthesis to the first holder component 12, complicating the procedure for releasing the prosthesis from the holder.

Figure 3:
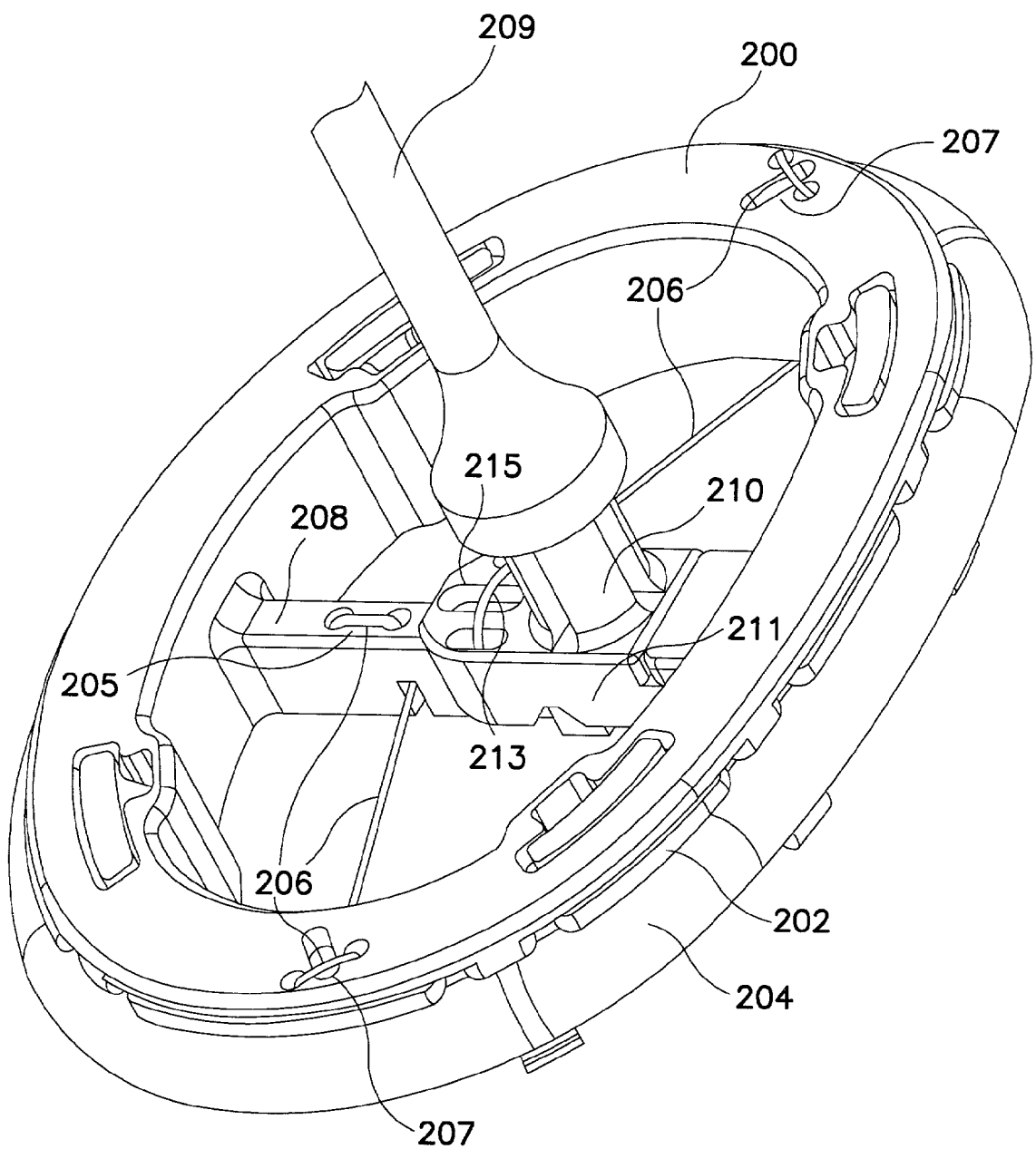
FIG. 3 is a perspective view of a two-component annuloplasty prosthesis holder according and associated handle according to a preferred embodiment of the present invention.

FIG. 3 is a perspective view of a second embodiment of a two-piece holder according to the present invention, with handle 209 attached. In this embodiment, annuloplasty prosthesis 204 is mounted against an outer circumferential surface of first holder component 202, which is in turn retained against second holder component 200. The second holder component 20 is provided with a snap fitting 210, engaging a pin on the end of the handle 209. The snap fitting may be replaced by a threaded recess or other mechanical mechanism for connecting to the handle 209. Snap fitting 210 is mounted to a removable base 211, which is retained to cross bar 208 of component 200 by means of suture 213, which is captured to base 211. Handle 209 and base 211 are removed together after cutting suture 213 at slot 215. Sutures 206 retain component 200 adjacent component 202. Sutures 206 are tied to component 200 in the vicinity of grooves 207 and 205. When cut at grooves 207, component 200 is released to move upward relative to component 202, in turn releasing the annuloplasty prosthesis 204, as described in more detail below.

In this view it can seen that substantial apertures are defined through the assembly comprising components 200 and 202, allowing for testing of the coaption of valve leaflets. The portions of sutures 206 extending across the apertures, between the edges of component 200 and cross bar 208 serve as a suturing guide to assist the physician in repair of leaflets with damaged chordae tendinae, as discussed in more detail in conjunction with FIGS. 8A and 8B.

Figure 4:
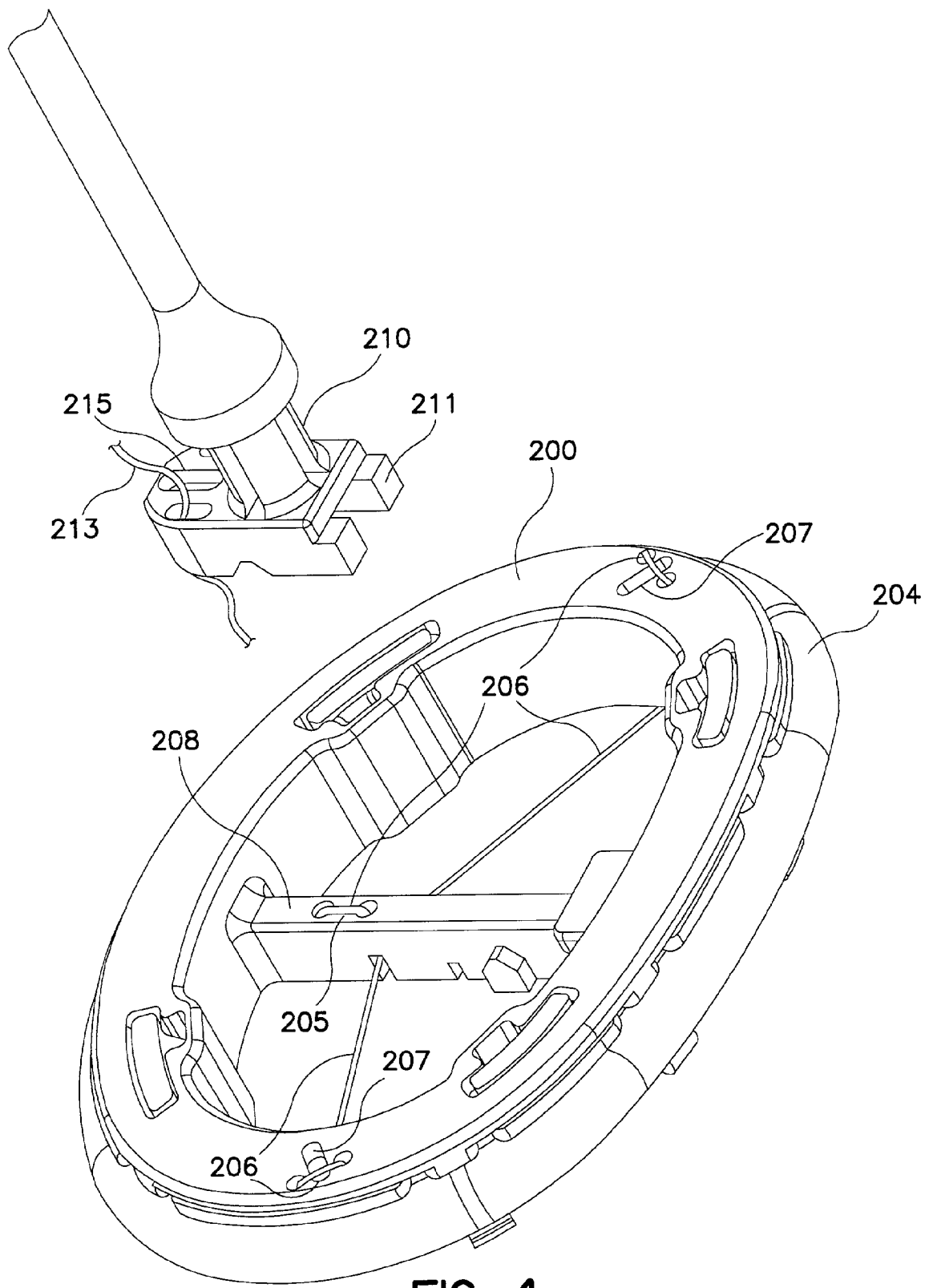
FIG. 4 is a perspective view from above of the embodiment of FIG. 3, with the handle removed.

FIG. 4 is a perspective view from above of holder components 202 and 200 and prosthesis 204 as illustrated in FIG. 3 showing removal of the handle 209 and base 211 after cutting of suture 213. While the preferred embodiment as illustrated employs a relatively small base 211 to which the handle is mounted, in alternative embodiments a template as discussed in conjunction with FIGS. 1 and 2, held to component 200 by cuttable sutures, might be substituted for base 211. Alternatively, base 211 might be omitted and snap fitting 210 might instead be formed as part of the crossbar 208. In yet other alternative embodiments some or all of crossbar 208 might be replaced with an additional suturing guide. In some such embodiments, the snap fitting 210 might be mounted adjacent to the inner periphery of component 200.

Figure 5:
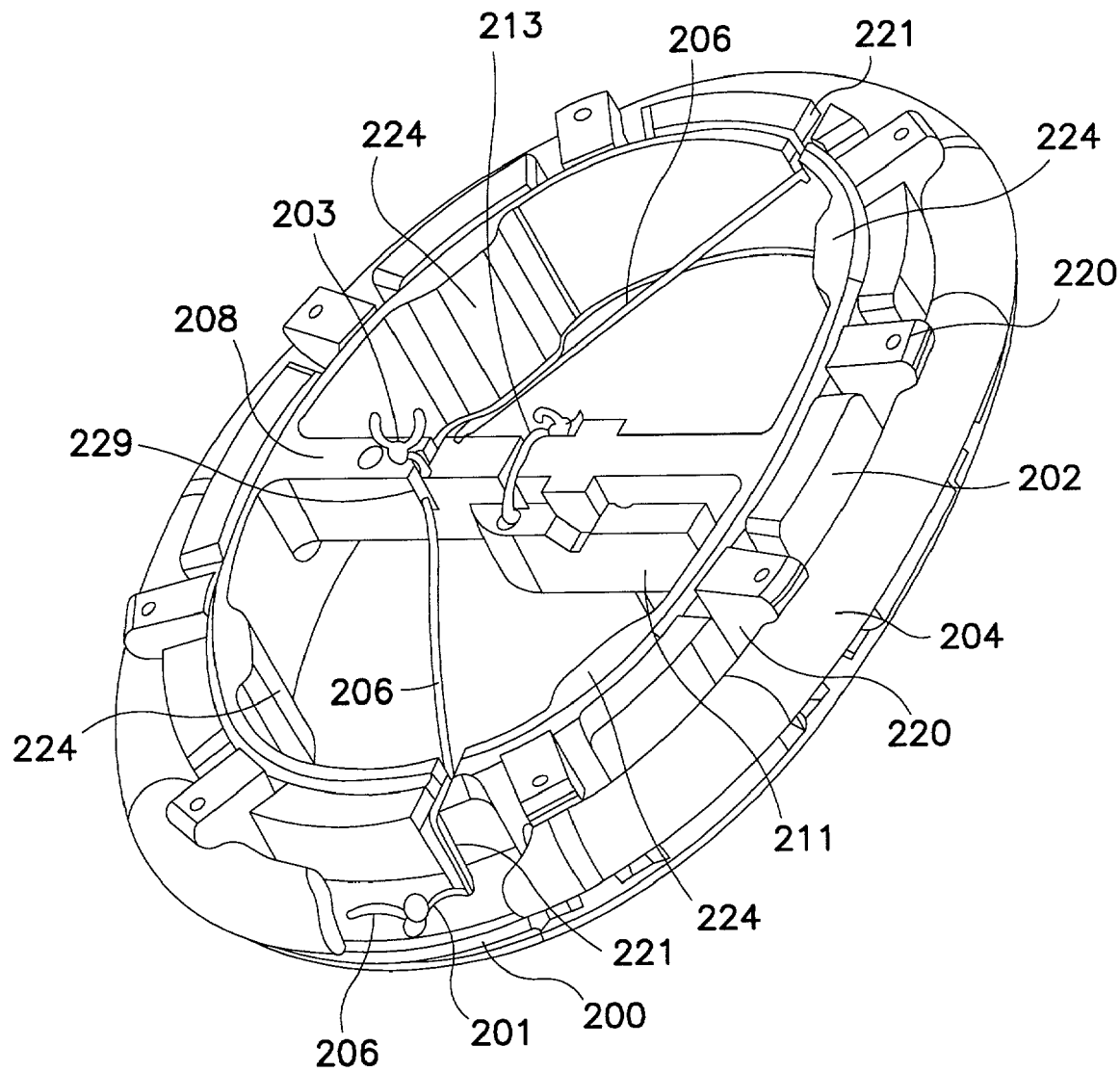
FIG. 5 is a perspective view from below of the embodiment of FIG. 3.

FIG. 5 is a view from below of the first and second holder components 202 and 200 in conjunction with the annuloplasty prosthesis 204. Numbered elements correspond to those in FIG. 3. In this view, the routing of the sutures 206 to retain first and second holder components 202, 200 closely adjacent to one another is further illustrated. Sutures 206 are tied to component 202 adjacent its outer periphery by knots 201, of which only one is visible. Free ends of sutures 206 then extend upward through component 200, across slots 207 (FIG. 3), back downward through component 200, along L-shaped slots 221 and across the apertures through component 202 to slot 229 in crossbar 208. Sutures 206 then pass upward through crossbar 208, along slot 205 (FIG. 7) back downward through crossbar 208 and are tied at knots 203 to retain them to the crossbar.

In operation, the first and second components of the holder work as follows. When first and second holder components 202, 200 are located closely adjacent to one another as illustrated, pins 214 (not visible in this view) extending downward from component 200 extend through prosthesis 204. Projections 220 extend radially outward from the first holder component 202 adjacent the lower surface of prosthesis 204 preventing downward movement of the prosthesis off of pins 214. This mechanical interrelation is illustrated in more detail in FIGS. 10 and 11A, discussed below. When released, component 200 can move upwardly enough to withdraw the pins 214 from prosthesis 204. Projections 220 are configured to allow them to bend inwardly after upward movement of component 200, facilitating removal of the prosthesis 204. This mechanism is also discussed in more detail in conjunction with FIGS. 6 and 7A. Holder components 200 and 202 are mechanically captured to one another by means of interacting tabs and grooves in regions 224 of the holder, described in more detail in conjunction with FIG. 7B.

Figure 6:
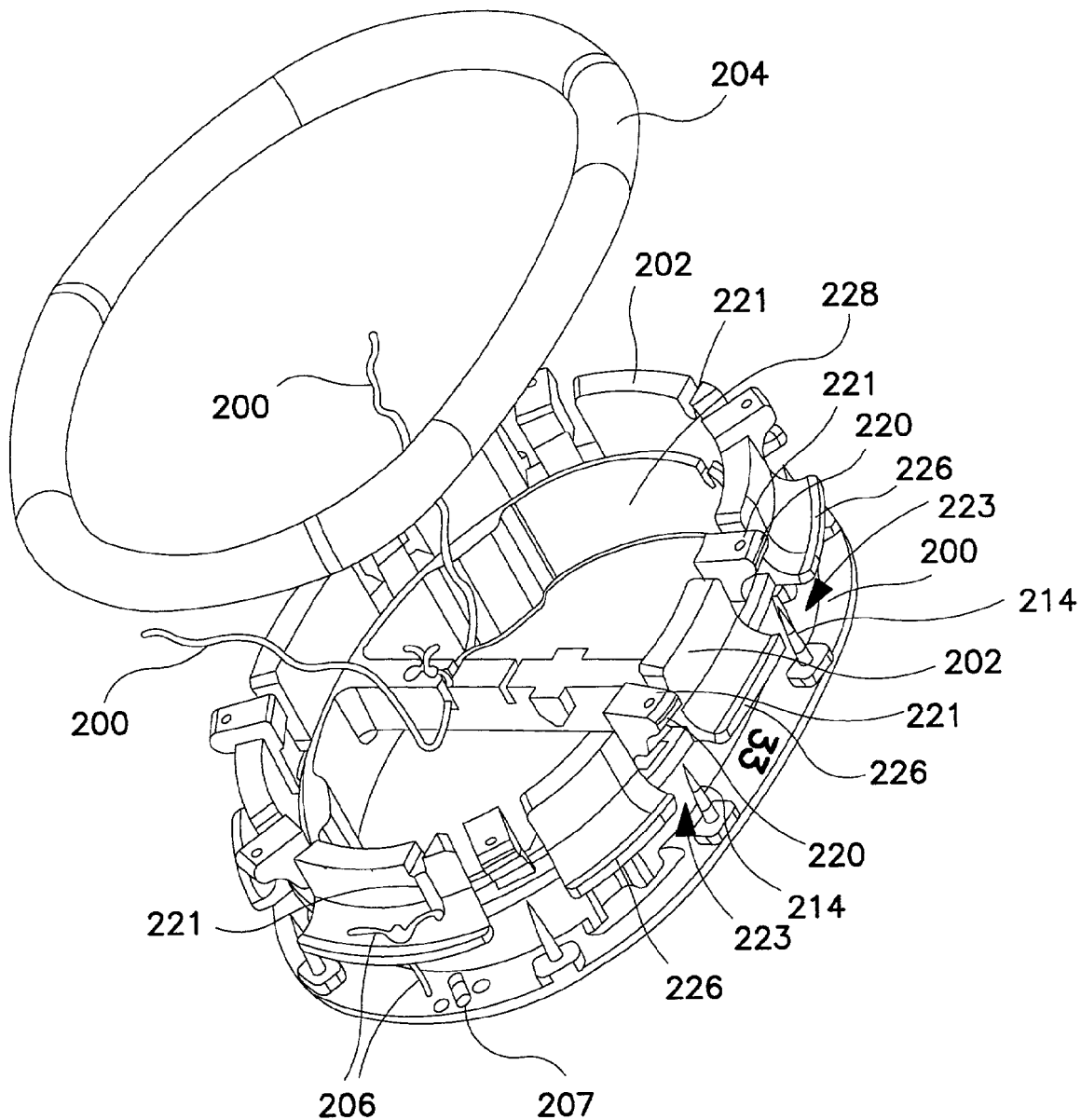
FIG. 6 is a perspective view from below of the embodiment of FIG. 3, illustrating the second component moved upwardly from the first component to release the annuloplasty prosthesis.

FIG. 6 is a view from below of the first and second holder components 202 and 200 in conjunction with the annuloplasty prosthesis 204. Numbered elements correspond to those in FIGS. 3–5. In this view, sutures 206 have been cut at slots 207, allowing for holder component 200 to be moved slightly upwardly from holder component 202. Holder component 200 has moved upwardly enough to withdraw pins 214 from prosthesis 204. The prosthesis 204 is removed over projections 220, leaving it positioned adjacent to valve annulus. In this view, it can be seen that pins 214 extend through openings or interruptions 223 in the circumferential flange 226 located adjacent the upper edge of component 202. As illustrated in more detail in FIG. 7A, projections 220 can pivot inwardly, facilitating removal of the prosthesis 204 from the holder after circumferential wall 228 of component 200 has moved upward of the projections 220 and no longer prevents their inward motion.

In the specific embodiment illustrated, pins 214 extend all the way through the prosthesis 204 and into corresponding holes 221 in the lower, radially extending projections 220. In other embodiments, pins 214 may be shortened and need not extend all the way to or into the lower radially extending projections 220. As discussed above, extension of the pins 214 to or preferably into the projections 120 may be especially desirable if the annuloplasty prosthesis 204 is very flexible and or extensible and may be less beneficial if the annuloplasty prosthesis 204 is a generally rigid or inextensible prosthesis. While the prosthesis 204 as illustrated takes the form of an annuloplasty ring, the holder may also be used with a band. In such case, the pins 214 are preferably located so that they will pass through the band adjacent its ends.

Figure 7A:
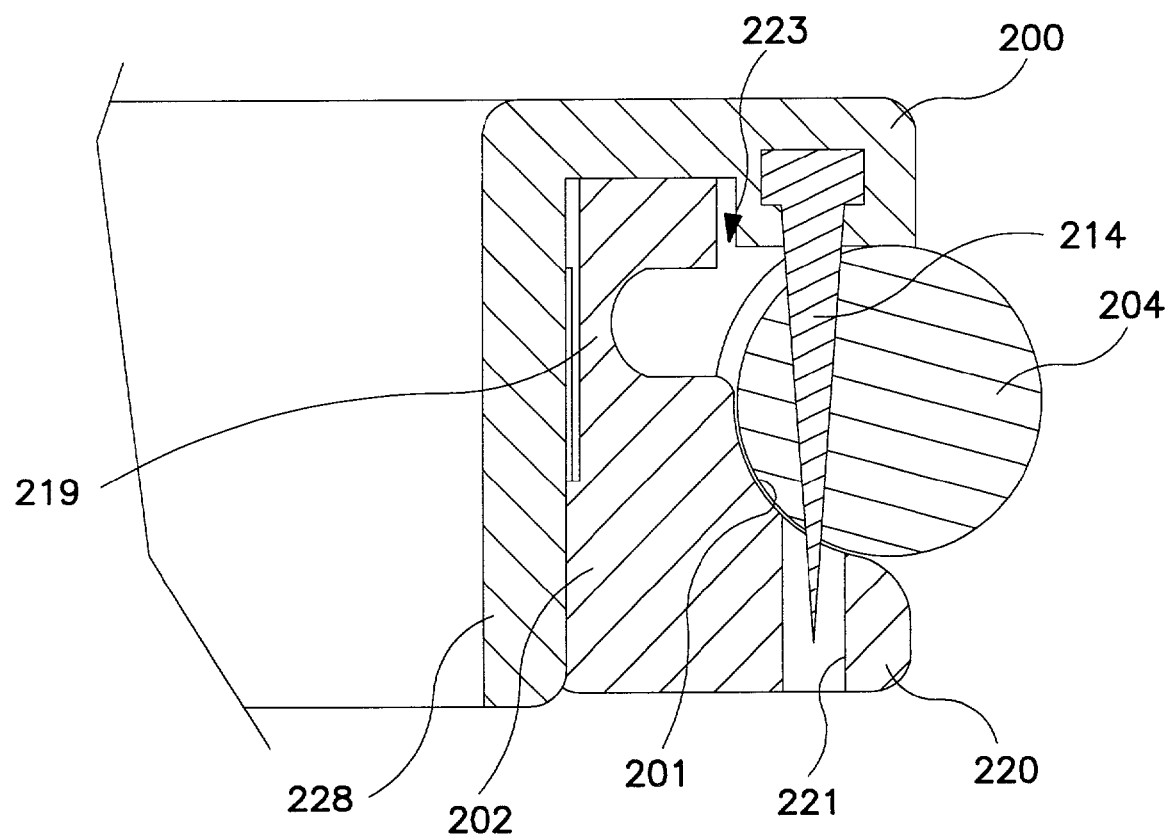
FIGS. 7A and 7B are a cross sectional views through portions of the first and second components of the embodiment of FIG. 3, illustrating interconnection of the prosthesis and the holder components.

FIG. 7A illustrates a cross-sectional view through a portion of the combination of first holder component 200, second holder component 202 and the prosthesis 204. In this view, illustrating the situation prior to upward movement of the second holder component. Pin 214 passes through the aperture 223 in the outwardly extending flange 226 (FIG. 6) of upper component 220, extends through prosthesis 204 and terminates in hole 221 in projection 220. Outwardly extending projection 220 prevents downward movement of the prosthesis 204 off of pin 214. Preferably, the thickness of first component 200 is reduced at 219 to define a hinge point, allowing projection 220 to pivot inward after upward movement of circumferential wall 228 has occurred.

Figure 7B:
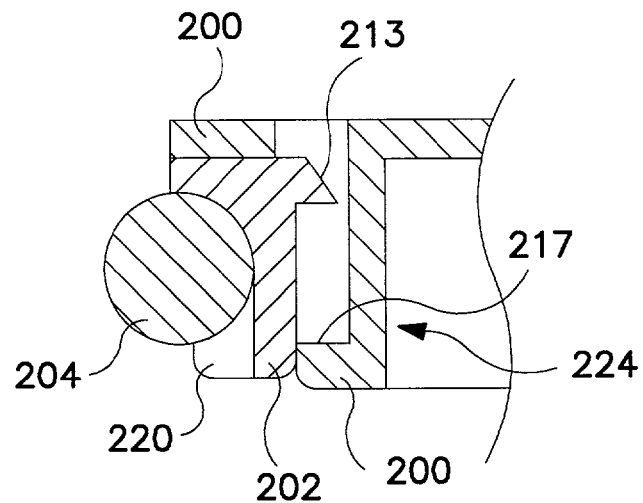

FIG. 7B illustrates a cross-sectional view of a portion of the assembly comprising first and second holder components 202, 200 and prosthesis 204. This cross-section is taken through one of the regions 224 illustrated in FIGS. 5 and 6. Holder components 200 and 202 are retained to one another by projections or tabs 213 located slidably within grooves 215, allowing upward movement of second component 200 until the lower end of 217 of groove 215 contacts the projection 213. This mechanism limits upward movement of the second holder component 200 and retains first and second holder components 200, 202 together, as illustrated in FIG. 6.

Figure 8A:
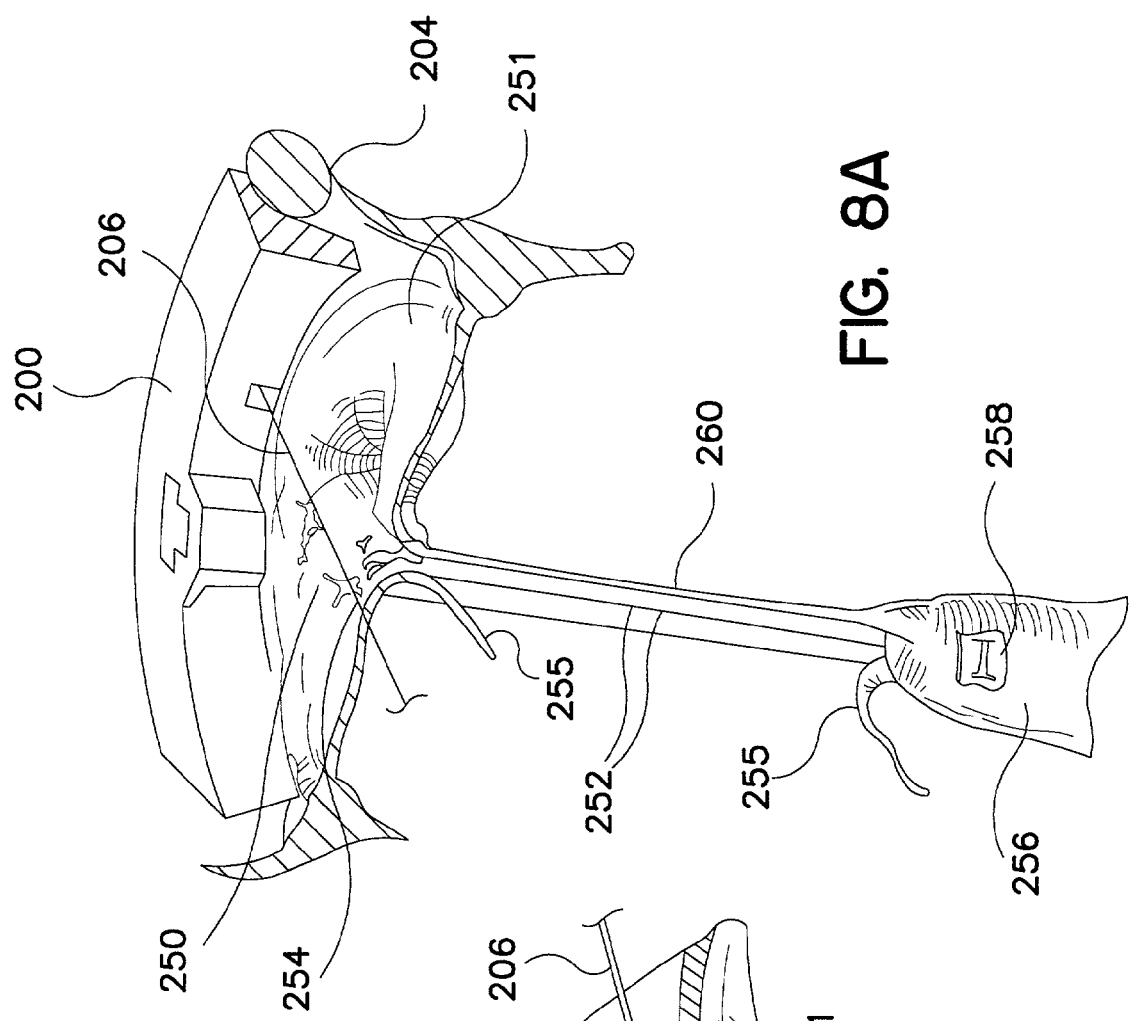
FIGS. 8A and 8B are cut-away views illustrating the use of the holder of FIG. 3 in conjunction with a surgical repair procedure.
Figure 8B:
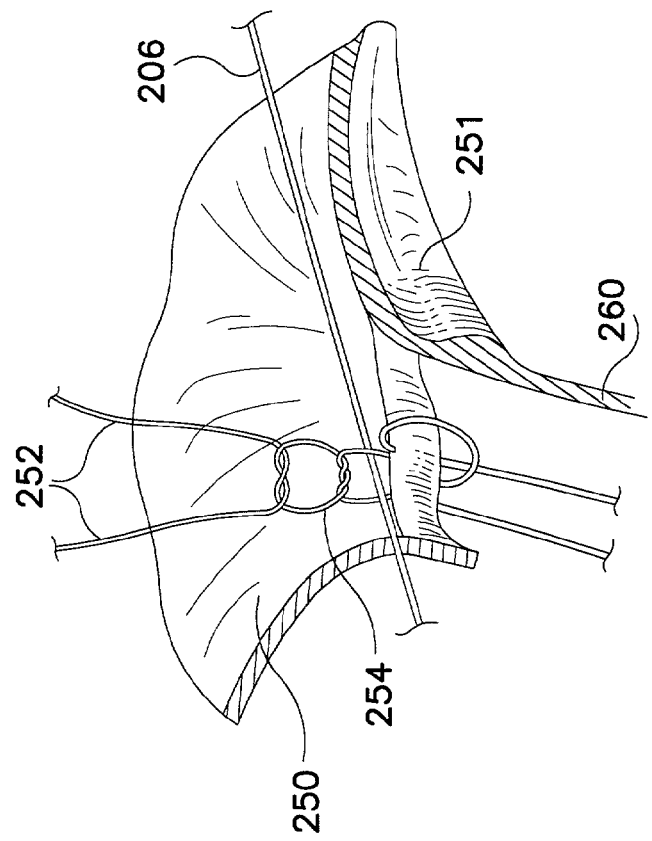

FIGS. 8A and 8B are cut-away views illustrating the utility of sutures 206 in conjunction with surgical repair of broken or elongated chordae tendinae (chords), as is sometimes performed in conjunction with placement of an annuloplasty prosthesis. The basic procedure involved is described in the article "Surgical Techniques For The Repair Of Anterior-Mitral Leaflet Prolapse" by Duran, published in the Journal Of Cardiovascular Surgery, 1999; 14:471–481, incorporated herein by reference in its entirety. As illustrated in FIG. 8A, a double-armed suture 252 is first attached to the papillary muscle 256 by means of a pledget 258. Alternatively, as described in the Duran article, if multiple chords are to be replaced, a loop of suture may be attached to the papillary muscle and multiple double-armed sutures passed through the loop for attachment to the valve leaflet or leaflets. Suture 252 is intended to replace the broken chord 255. The free ends of the suture 252 are passed upward and sutured to the edge of valve leaflet 250, previously attached to the papillary muscle 256 by means of the broken chord.

In the procedure as described in the above cited Duran article, adjustment of the height of the leaflet 250 to determine proper placement of knots 254, coupling the sutures 252 to the leaflet 250 was accomplished by means of an additional suture passed through the leaflet, held upward by means of forceps to adjust the appropriate leaflet height. In conjunction with the present invention, after the annuloplasty prosthesis 204 has been moved downward and sutured to the valve annulus, suture 206 is used as a suturing guide for determining the proper point at which knots 254 are tied, to assure that the leaflet 250 will coapt properly with the adjacent leaflet 251. Knots 254 comprise a series of knots, the first of which is tied around suture 206. The remaining knots are tied thereafter. One or more repairs of this type may be made along the portions of suture 206 extending across the apertures through the annuloplasty prosthesis holder, depending upon the number of chords that are broken. In the embodiment as illustrated in FIGS. 3-5 above, the path of the sutures 206 as they cross the apertures through the annuloplasty holder is intended to generally approximate the line of coaption of the leaflets of a mitral valve, facilitating their use in this particular surgery. Other possible routings for the sutures 206 might be substituted in conjunction with other possible valve repair surgeries.

FIG. 8B illustrates the production of knots 254 to anchor sutures 252 to the valve leaflet 250 in more detail. In this view it can be seen that one of the free ends of the suture 252 is passed upward through the valve leaflet, around the edge of the valve leaflet and through the leaflet again, while the other free end is simply passed up through the valve leaflet. The free ends are knotted together around suture 206 and the series of knots is continued until an adequate number of knots are provided to safely anchor the suture 252 to the valve leaflet 250.

After the leaflet repair is complete, sutures 206 are cut at slots 207 (FIG. 3) as discussed above to allow annuloplasty holder component 200 to move upward relative to component 202 (FIG. 6) to release the prosthesis 204. This also allows the cut ends of the sutures 206 to be pulled through the knot or knots 254, as the holder assembly is moved upward away from the valve annulus. While sutures 206, provide a preferred mechanism for facilitating the repair procedure discussed above, it is possible that other structures could be substituted for them, including other types of tensile members or more rigid members such as rods or bars, provided that provision is made for removal of the structures from the knots 254, after the surgical repair is complete.

Figure 9:
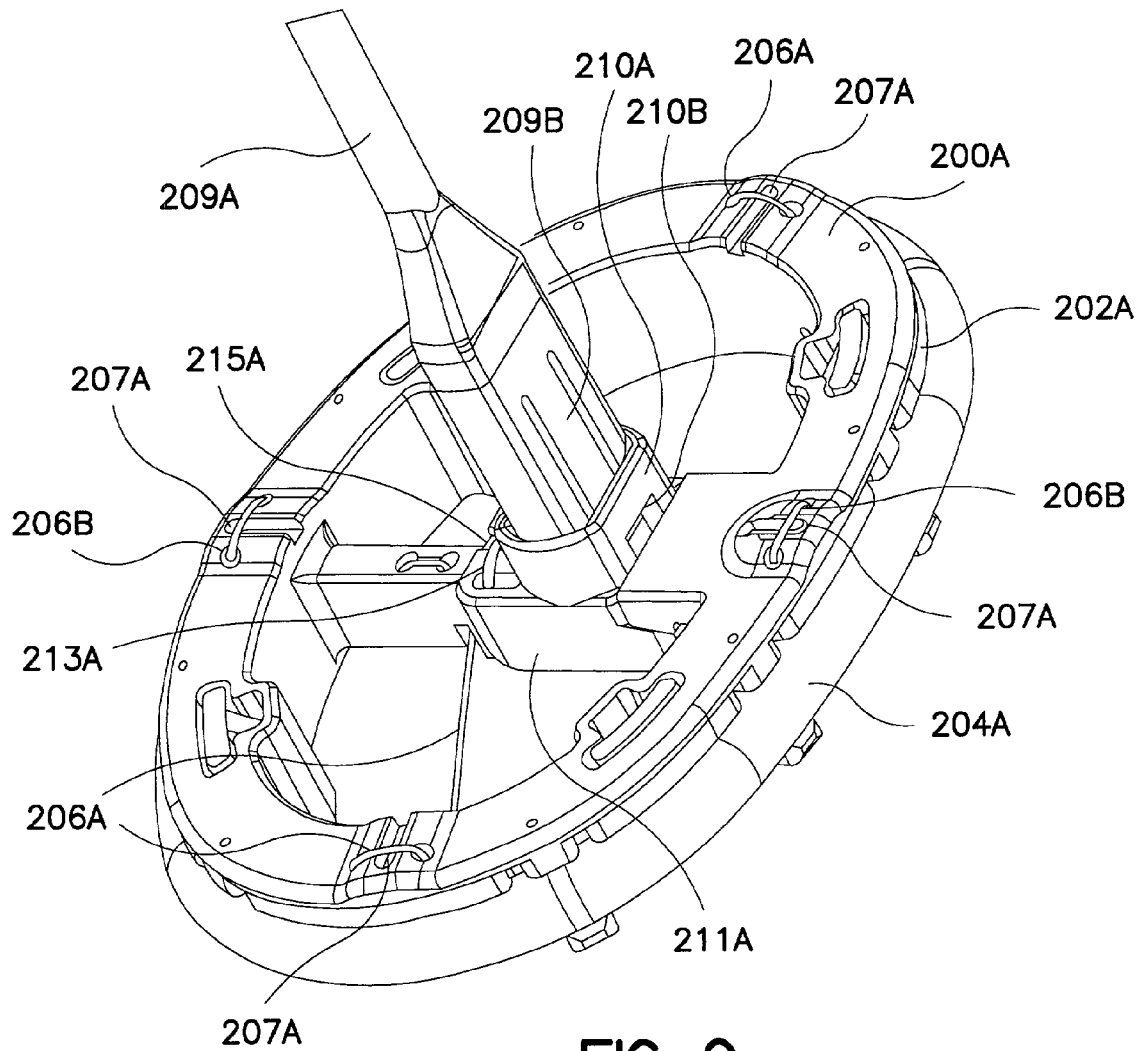
FIG. 9 is a perspective view of a second embodiment of two-component annuloplasty prosthesis holder according and associated handle according to a preferred embodiment of the present invention.

FIG. 9 is a perspective view of an alternative embodiment of the present invention which operates in the same general manner as the embodiment illustrated in FIGS. 3-8B, described above. The embodiment of FIG. 9 does include some differences in structure and function, which are discussed in more detail below.

The handle 209A is somewhat modified from the handle illustrated in FIG. 3, in that the lower end of the handle is provided with two inwardly deflectable arms 209B, each carrying an outwardly extending projection at their lower end, engaging in corresponding apertures 210B in snap fitting 210A. Base member 211A otherwise corresponds generally to base member 211 discussed above, and is secured to holder component 200A by means of suture 215A in the same fashion as described in conjunction with base member 211 described above.

The suturing guide 206A takes the form of a cuttable suture, routed in a manner analogous to that of the above-described embodiment. However, cutting guides 207A are formed as grooves in the upper surface of component 200A rather than penetrating through the component. Further, two additional retention sutures 206B are provided, which operate to retain component 200A to component 202A, in addition to the retention function performed by the sutures 206A. Sutures 206B are also associated with cutting guides 207A, which take the form of slots formed in the upper surface of component 200A. Cutting of the sutures 206A and 206B at all four of the cutting guides 207A is required in order for component 202A to be moved downward relative to component 200A to release the prosthesis 204A, in a manner analogous to that described in conjunction with the embodiment discussed above.

Figure 10:
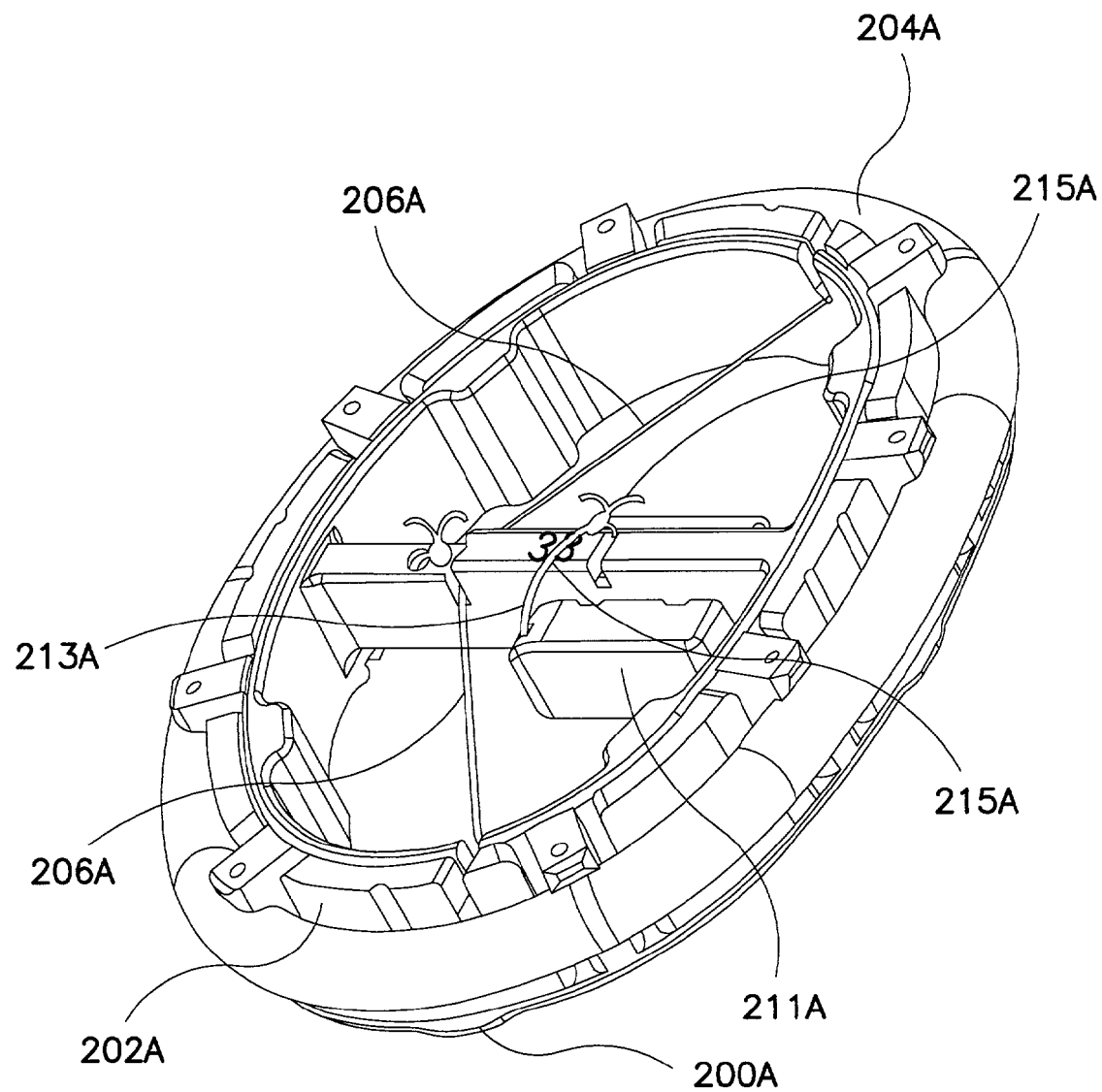
FIG. 10 is a perspective view from below of the embodiment of FIG. 9.

FIG. 10 is a perspective view from the lower surface of the embodiment of FIG. 9. All numbered components correspond to identically numbered components illustrated in FIG. 9, discussed above.

Figure 11:
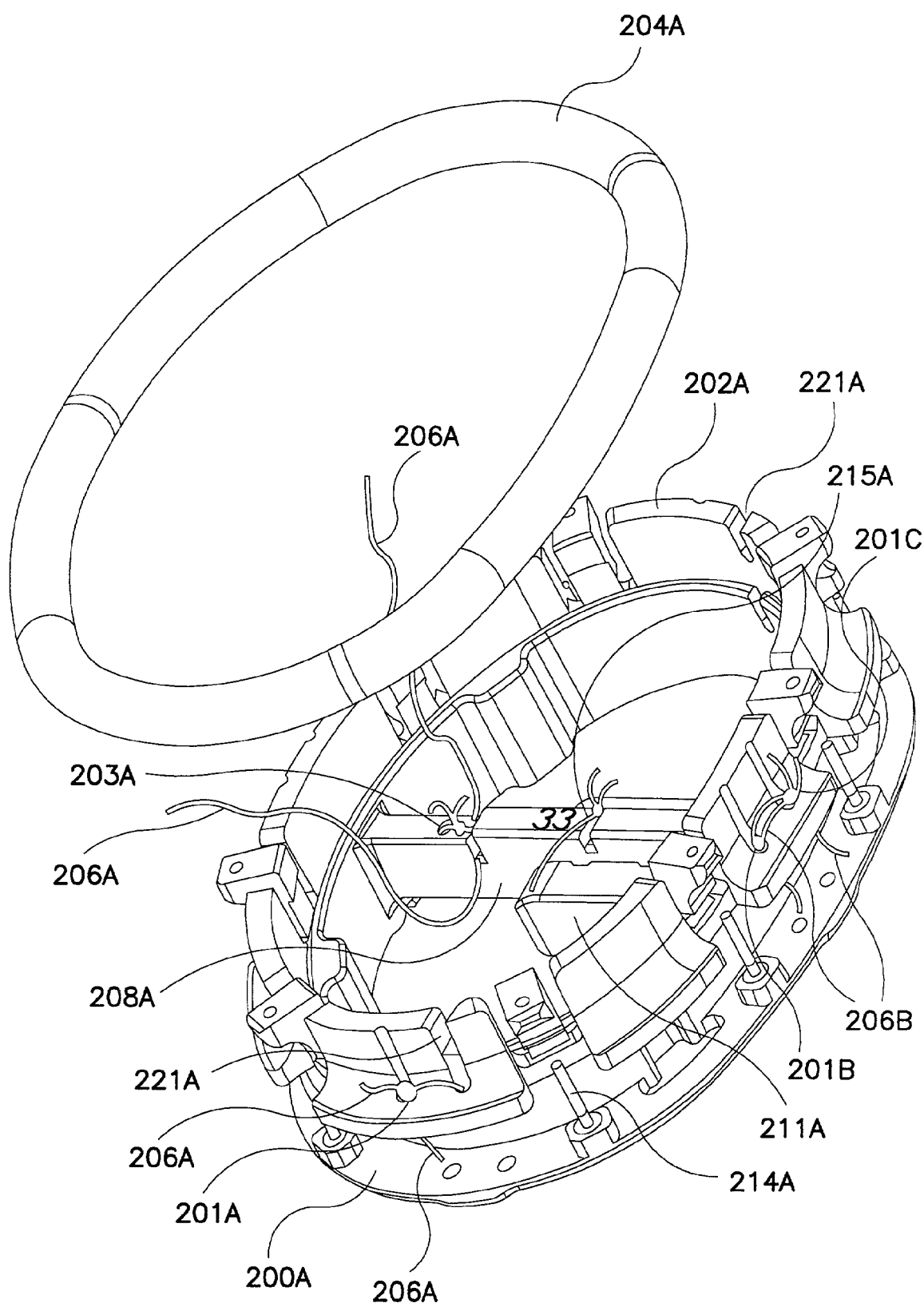
FIG. 11 is a perspective view from below of the embodiment of FIG. 9, illustrating the second component moved upwardly from the first component to release the annuloplasty prosthesis.

FIG. 11 is a perspective view from below the embodiment of FIG. 9 with component 202A moved downward relative to component 200 to release prosthesis 204A. In order for component 200A to move downward relative to component 200A, all of the sutures 206A and 206B must be cut at cutting guides 207A (FIG. 9).

In this view, the routing of sutures 206A and 206B is more clearly illustrated. Sutures 206A are anchored to component 202A by passing them through two adjacent holes in component 202A and knotting the sutures at 201A to retain them to component 202A. One end of each suture 206A is then passed upward through adjacent holes the components 202A and 200A, extended across a cutting guide 207A (FIG. 9), passed downward through adjacent holes in components 200A and 202A on the other side of cutting guide 207A and passed through slot 221A. The sutures 206A are then extended across the aperture through component 202A, where they are anchored to crossbar 208A by means of knot 203A in a manner identical to that described in conjunction with the embodiment of FIGS. 3-8B. Sutures 206B are first anchored to component 202A by being looped through adjacent holes through component 202A and knotted at 201B. One free end of each suture 206B is then passed upward through adjacent holes in components 202A and 200A, extended across a cutting guide 207A (FIG. 9), passed downward through adjacent holes in components 200A and 202A on the other side of cutting guide 207A and knotted at 201C to retain components 200A and 202A adjacent to one another. As illustrated, the free ends of the suture 206B are shown after cutting to allow downward movement of component 202A relative to component 200A.

In this view it can also be seen that the needles 214A, rather than being provided with sharp tips as in the embodiment of FIGS. 3-8 described above, are provided with rounded or ball-tip ends. The needles 214A pass through prosthesis 204A and operate to retain the prosthesis to the holder in the same manner as described above in conjunction with the embodiment of FIGS. 3-8B.

We claim:

1. An annuloplasty system for use in repairing a heart valve having leaflets and a valve annulus, comprising:
   a first holder component having a central opening, an upper surface, a lower surface and a circumferential surface corresponding generally to the configuration of the valve annulus;
   an annuloplasty prosthesis, located adjacent to and extending at least partially around the circumferential surface;
   at least one rigid downwardly extending penetrating member mounted to the holder and extending into the prosthesis and holding it adjacent the circumferential surface; and
   a suturing guide extending across the central opening along a path approximating a line of leaflet coaption of the heart valve.

2. A system as in claim 1, wherein the prosthesis is a flexible annuloplasty prosthesis.

3. A system as in claim 1, wherein the circumferential surface comprises at least one outwardly extending member preventing the prosthesis from moving downward and off of the penetrating member.

4. A system as in claim 3 wherein the outwardly extending member is located below the downwardly extending member.

5. A system as in claim 3 wherein the at least one downwardly extending member comprises a plurality of downwardly extending members and wherein the at least one outwardly extending member comprises a plurality of outwardly extending members, located below respective ones of the penetrating members.

6. A system as in claim 3 wherein the penetrating member extends into the outwardly extending member, preventing the prosthesis from moving downward and off of the penetrating member.

7. A system as in claim 3 wherein the at least one downwardly extending member comprises a plurality of penetrating members and wherein the at least one outwardly extending member comprises a plurality of outwardly extending members, into which respective ones of the penetrating members extend.

8. A system as in claim 3 wherein the at least one downwardly extending member comprises a plurality of penetrating members and wherein the at least one outwardly extending member extends around a portion the circumferential surface and is located below a plurality of the penetrating members.

9. A system as in claim 1, wherein the holder comprises a second holder component, coupled to and extending above the first holder component.

10. A system as in claim 9, wherein the at least one penetrating member is mounted to the second holder component.

11. A system as in claim 10, wherein the second holder component is movable upwardly relative to the first holder component to withdraw the penetrating member from the prosthesis.

12. A system as in claim 11, wherein the second holder component is releasably secured adjacent to the first holder component, temporarily preventing upward movement of the second holder component.

13. A system as in claim 11, wherein the second holder component is releasably secured to the first holder component by a cuttable suture.

14. A system as in claim 13, wherein the suturing guide comprises a portion of the cuttable suture.

15. A system as in claim 11, comprising means for retaining the second holder component to the first holder component after upward movement of the second holder component.

16. A system as in claim 1, wherein the suturing guide is a cuttable suture.

17. An annuloplasty system for use in repairing a heart valve having leaflets and a valve annulus, comprising:
   a first holder component having a central opening, an upper surface, a lower surface and a circumferential surface corresponding generally to the configuration of the valve annulus;
   an annuloplasty prosthesis, located adjacent to and extending at least partially around the circumferential surface;
   a suturing guide extending across the central opening along a path approximating a line of leaflet coaption of the heart valve,
   wherein the suturing guide is a cuttable suture; and
   further comprising a second holder component, wherein the second holder component is retained closely adjacent to the first holder component by the cuttable suture.

18. A system as in claim 17 wherein the cuttable suture is routed so that upon cutting the cuttable suture, the first and second holder components may be moved apart from one another.

19. A system according to claim 18 wherein movement of the first and second holder components away from one another allows removal of the annuloplasty prosthesis from the holder.

* * * * *